United States Patent
Van Der Heiden

(10) Patent No.: US 9,474,220 B2
(45) Date of Patent: Oct. 25, 2016

(54) **FRUITS OF THE GENUS *CAPSICUM***

(71) Applicant: Enza Zaden Beheer B.V., Enkhuizen (NL)

(72) Inventor: Anton Arnold Van Der Heiden, Enkhuizen (NL)

(73) Assignee: ENZA ZADEN BEHEER B.V., Enkhuizen (NL)

( * ) Notice: Subject to any disclaimer, the term of this patent is extended or adjusted under 35 U.S.C. 154(b) by 0 days.

(21) Appl. No.: 14/300,129

(22) Filed: Jun. 9, 2014

(65) Prior Publication Data

US 2014/0289885 A1    Sep. 25, 2014

Related U.S. Application Data

(63) Continuation of application No. 10/552,969, filed as application No. PCT/EP03/03987 on Apr. 14, 2003, now abandoned.

(51) Int. Cl.
*A01H 5/08* (2006.01)
*A01H 1/02* (2006.01)
*A01H 1/04* (2006.01)
*A01H 1/00* (2006.01)

(52) U.S. Cl.
CPC *A01H 5/08* (2013.01); *A01H 1/02* (2013.01); *A01H 1/04* (2013.01)

(58) Field of Classification Search
None
See application file for complete search history.

(56) References Cited

U.S. PATENT DOCUMENTS

| | | | |
|---|---|---|---|
| 5,262,316 | A | 11/1993 | Engler et al. |
| 5,523,520 | A | 6/1996 | Hunsperger et al. |
| 5,959,186 | A | 9/1999 | Arevalos et al. |
| 6,124,528 | A | 9/2000 | Shewmaker |
| 6,498,287 | B2 | 12/2002 | Nash |
| 7,642,423 | B2 | 1/2010 | Nicolet et al. |
| 8,026,424 | B2 | 9/2011 | Van Der Heiden |
| 8,044,273 | B2 | 10/2011 | Van Der Heiden |
| 8,067,681 | B2 | 11/2011 | Van Der Heiden |
| 8,338,672 | B2 | 12/2012 | Lindeman |
| 8,536,419 | B2 | 9/2013 | Lindeman |
| 8,618,370 | B2 | 12/2013 | Lindeman et al. |
| 8,816,170 | B2 | 8/2014 | Aardse |
| 9,089,099 | B2 | 7/2015 | Sances Lopez |
| 2006/0059585 | A1 | 3/2006 | Jankowski et al. |
| 2006/0195921 | A1 | 8/2006 | Van Der Heiden |
| 2009/0019561 | A1 | 1/2009 | Van Der Heiden |
| 2009/0019599 | A1 | 1/2009 | Van Der Heiden |
| 2009/0019600 | A1 | 1/2009 | Van Der Heiden |
| 2009/0313713 | A1 | 12/2009 | Lindeman |
| 2011/0197313 | A1 | 8/2011 | Lindeman |
| 2012/0066797 | A1 | 3/2012 | Lindeman et al. |
| 2013/0024962 | A1 | 1/2013 | Aardse |
| 2014/0223611 | A1 | 8/2014 | Lindeman et al. |
| 2014/0230084 | A1 | 8/2014 | Sances Lopez |
| 2014/0259195 | A1 | 9/2014 | Lindeman |
| 2014/0283167 | A1 | 9/2014 | Sances Lopez |
| 2015/0264877 | A1 | 9/2015 | Sances Lopez |

FOREIGN PATENT DOCUMENTS

WO    01/62075 A2    8/2001

OTHER PUBLICATIONS

Final Office Action received for U.S. Appl. No. 10/552,969, mailed on Apr. 14, 2011, 11 pages.
Final Office Action received for U.S. Appl. No. 10/552,969, mailed on Sep. 8, 2009, 7 pages.
Non Final Office Action received for U.S. Appl. No. 10/552,969, mailed on Aug. 15, 2013, 12 pages.
Non Final Office Action received for U.S. Appl. No. 10/552,969, mailed on Apr. 15, 2008, 12 pages.
Non Final Office Action received for U.S. Appl. No. 10/552,969, mailed on Nov. 5, 2008, 10 pages.
Non Final Office Action received for U.S. Appl. No. 10/552,969, mailed on Oct. 7, 2010, 9 pages.
Restriction Requirement Received for U.S. Appl. No. 10/552,969, mailed on Jan. 8, 2008, 6 pages.
Advisory Action received for U.S. Appl. No. 10/552,969, mailed on Dec. 15, 2009, 3 pages.
Final Office Action received for U.S. Appl. No. 10/552,969 mailed on Apr. 7, 2014, 7 pages.
Notice of Allowance received for U.S. Appl. No. 12/704,229, mailed on Aug. 2, 2012, 8 pages.
Final Office Action received for U.S. Appl. No. 11/776,013, mailed on Mar. 23, 2011, 8 pages.
Non Final Office Action received for U.S. Appl. No. 11/776,013, mailed on Nov. 9, 2010, 12 pages.
Notice of Allowance received for U.S. Appl. No. 11/776,013, mailed on May 27, 2011, 7 pages.
Final Office Action received for U.S. Appl. No. 12/139,795, mailed on Sep. 26, 2011, 7 pages.
Non Final Office Action received for U.S. Appl. No. 12/139,795, mailed on Apr. 19, 2011, 14 pages.
Notice of Allowance received for U.S. Appl. No. 12/139,795, mailed on Jun. 24, 2013, 9 pages.
Notice of Allowance received for U.S. Appl. No. 11/776,008, mailed on Jun. 10, 2011, 6 pages.

(Continued)

*Primary Examiner* — Phuong Bui

(74) *Attorney, Agent, or Firm* — Morrison & Foerster LLP

(57) ABSTRACT

The present invention relates to a method for obtaining fruits of plants of the genus *Capsicum* with improved taste and enriched nutritional value and especially to fruits with increased sucrose and/or ascorbic acid content as compared to plants of a similar type. The method involves manipulation of the CL and the Y loci of plants of the genus *Capsicum*.

4 Claims, 2 Drawing Sheets

(56) References Cited

OTHER PUBLICATIONS

Figure 1:
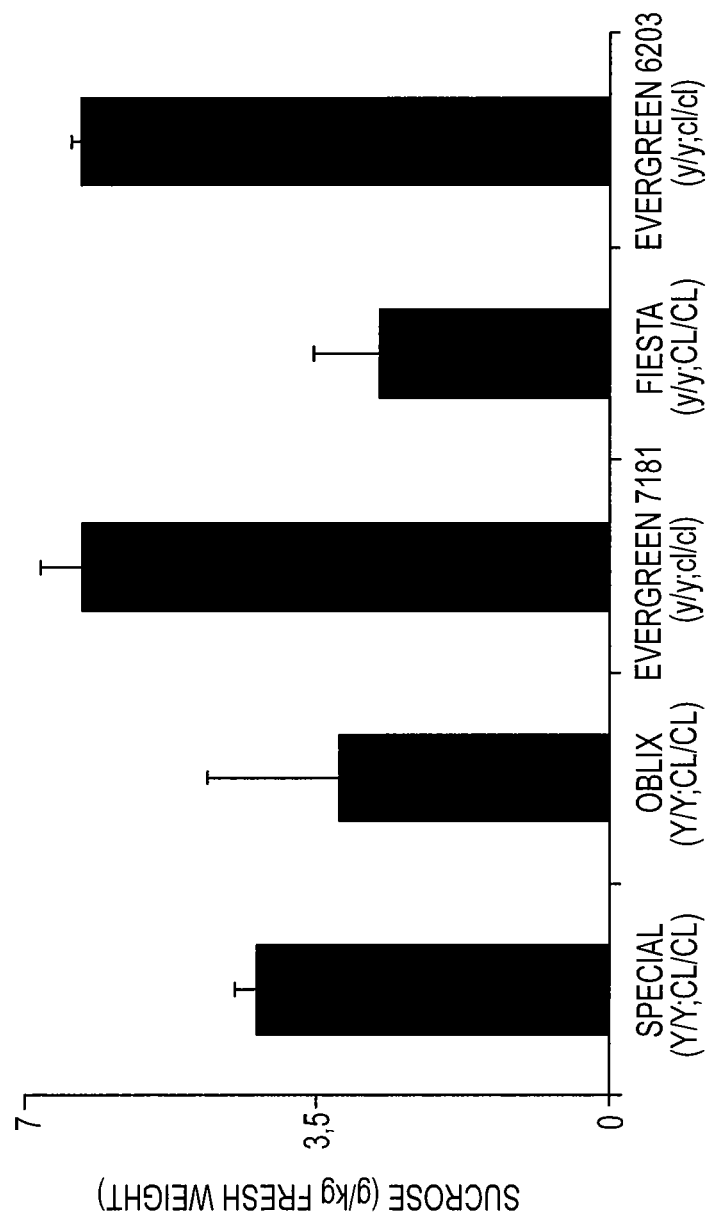

Final Office Action received for U.S. Appl. No. 11/776,008, mailed on Mar. 23, 2011, 8 pages.
Non Final Office Action received for U.S. Appl. No. 11/776,008, mailed on Nov. 9, 2010, 12 pages.
Non-Final Office Action received for U.S. Appl. No. 13/189,237, mailed on Feb. 25, 2014, 11 pages.
Notice of Allowance received for U.S. Appl. No. 13/189,237, mailed on Jun. 3, 2014, 5 pages.
Final Office Action received for U.S. Appl. No. 13/232,466, mailed on Jun. 24, 2013, 10 pages.
Non-Final Office Action received for U.S. Appl. No. 13/232,466, mailed on Dec. 21, 2012, 13 pages.
Notice of Allowance received for U.S. Appl. No. 13/232,466, mailed on Aug. 28, 2013, 8 pages.
Notice of Allowance received for U.S. Appl. No. 13/232,466, mailed on Oct. 28, 2013, 3 pages.
Non-Final Office Action received for U.S. Appl. No. 13/766,219, mailed on Feb. 3, 2015, 12 pages.
Notice of Allowance received for U.S. Appl. No. 13/766,219, mailed on Jun. 5, 2015, 5 pages.
Non-Final Office Action received for U.S. Appl. No. 13/794,476, mailed on May 7, 2015, 12 pages.
Notice of Allowance received for U.S. Appl. No. 13/794,476, mailed on Aug. 3, 2015, 5 pages.
"Database WPI, Section Ch, Week 20327", Derwent Publications Ltd., Antal, J., 'Kurtovszka Kapia' Capsicum Annum, Jan. 28, 2003, 1 page.
Bouw, Elbert, Unpublished U.S. Appl. No. 14/714,016, filed May 15, 2015, titled "Hybrid Pepper E2000043", 43 pages.
Enza Zaden Beheer B.V., "Database: Netherlands Applications for Plant Breeders Rights, Application No. PPS1238 E490264", Jan. 27, 2011, 2 pages.
Enza Zaden Beheer B.V., "Official Gazette of the Community Plant Variety Office 2010/6; Publication Notice for Application No. CPVR 20101771 Capsicum Annuum L.", Dec. 15, 2010, 3 pages.
Eshed et al., "Less-Than-Additive Epistatic Interactions of Quantitative Trait Loci in Tomato", Genetics, vol. 143, Aug. 1996, pp. 1807-1817.
Honma, S, "Capsicum Annuum Named MIGOLD, PI 586678", deposited 1986, 4 pages.
Jenkins, Merle, "The Segregation of Genes Affecting Yield of Grain in Maize", Journal of the American Society of Agronomy, vol. 21, 1940, pp. 55-63.
Kraft et al., "Linkage Disequilibrium and Fingerprinting in Sugar Beet", Theor. Appl. Genet., vol. 101, 2000, pp. 323-326.
Lefebvre et al., "The Capsanthin-Capsorubin Synthase Gene: A Candidate Gene for the Y Locus Controlling the Red Fruit Colour in Pepper", Plant Molecular Biology, vol. 36, 1998, pp. 785-789.
Molchova et al., "On the Interspecific Crossability Between Capsicum Annuum L. and Capsicum Pubescens R. & P.; Capsicum Annuum L. and Capsicum Pendulum Wild. (SIN BACCATUM)", Capsicum Newsletter, vol. 1, 1982, pp. 39-41.
Newman et al., "Synthesis of Two Chromoplast-Specific Proteins During Fruit Development in Capsicum Annuum", Plant Physiology, vol. 91, 1989, pp. 455-458.
Nikova et al., "Overcoming of Interspecies Incompatibility in the Solanaceaous Genera *Nicotiana* and *Capsicum* via In Vitro Techniques", In Vitro Cellular and Developmental Biology, Animal, vol. 37, No. 3, Part 2, 2001, p. 40A.
Onus, et al., "Monogenic Segregations in Backcross Progenies of Capsicum baccatum x Two Interspecific F1 Hybrids and Some Possible Explanations for Distorted Segregation Ratios in Capsicum", Turkish Journal of Botany, vol. 24, 2000, pp. 319-328.
Osuna-Garcia et al., "Endogenous Levels of Tocopherols and Ascorbic Acid during Fruit Ripening of New Mexican Type Chile (*Capsicum annuunt* L.) Cultivars", Journal of Agricultural and Food Chemistry, vol. 46, No. 12, 1998, pp. 5093-5096.
Oren-Shamir et al., "Occurrence of the Chromoplast Protein ChrA Correlates with a Fruit-Color Gene in Capsicum Annum", Plant Molecular Biology, vol. 21, 1993, pp. 549-554.
Poehlman et al., "Methods in Plant Breeding", In Breeding Field Crops, 4th ed., Iowa State University Press, 1995, pp. 172-174.
Park et al., "Susceptibilization of Red Pepper *Capsicum-annuum* L. to Colletotrichum-Gloeosporioides Penz. in Relation to the Ripening of Fruits", Korean Journal of Plant Pathology, vol. 5, No. 3, 1989, pp. 262-270.
Quiros, Carlos F., "Solanacea: Pepper: *Capsicum* spp", VC 221, online fact sheet from www.plantsciences.ucdavis.edu/vc221/pepper, Apr. 2003.
Sahin, et al., "Resistance in *Capsicum pubescens* to *Xanthomonas campestris* pv. *vesicatoria* Pepper Race 6", Plant Disease, vol. 82 No. 7, 1998, pp. 794-799.
Sances Lopez, Antonio, Unpublished U.S. Appl. No. 14/657,171, filed Mar. 13, 2015, titled "Hybrid Pepper E20S1012777", 42 pages.
Shifriss et al., "Studies of the Inheritance of Mature Fruit Color in Capsicum Annuum L.", Euphytica, vol. 60, 1992, pp. 123-126.
Simpson et al., "Chromoplast Ultrastructure of Capsicum Carotenoid Mutants II. Effect of Light and CPTA", Z Pflanzenphysiol. Bd., vol. 83, 1977, pp. 309-325.
Smith, Paul G., "Inheritance of Brown and Green Mature Fruit Color in Peppers", Journal of Heredity, vol. 41, No. 5, 1950, pp. 138-140.
Van Der Heiden, Anton A., Unpublished U.S. Appl. No. 12/961,222, filed Dec. 6, 2010, titled "Pepper Hybrid E490264".
Zijlstra et al., Pollen Tube Growth in Interspecific Crosses between Capsicum Species, HortScience, vol. 26, No. 5, 1991, pp. 585-586.
CPVR 2009/2170. Sweet46. Filed Oct. 23, 2009. Granted Apr. 23, 2012.
NL PBR PPS1165. Sweet46. Filed Oct. 23, 2009. Granted Jan. 27, 2012.

FRUITS OF THE GENUS *CAPSICUM*

CROSS REFERENCE TO RELATED APPLICATIONS

This application is a Continuation of U.S. patent application Ser. No. 10/552,969, filed Oct. 13, 2005, which is a U.S. National Phase patent application of PCT/EP2003/03987, filed Apr. 14, 2003, both of which are hereby incorporated by reference in the present disclosure in their entirety.

The present invention relates to a method for obtaining fruits of plants of the genus *Capsicum* with improved taste and enhanced nutritional value and especially to fruits with increased sucrose and/or ascorbic acid content as compared to plants of a similar type. The invention also relates to fruits, plants, plant parts and seeds of the genus *Capsicum* obtainable by said method and to the use of the fruits and especially the use of the fruits for the preparation of food products.

Fruits of plants of the genus *Capsicum*, like sweet peppers (paprika's) and hot peppers, hereafter both species are referred to as peppers, are available in a wide variety of different colors like red, yellow, brown, and orange for fully matured fruits and green, white, lilac, and purple for non-mature "unripe" fruits. In general, any random non-mature color can develop in any random mature color.

The color of the fruits is a result of a mixture of different color components in the fruit. The color component green is provided by the presence of chloroplasts containing an abundant amount of green chlorophyl. The color component red and yellow are provided by chromoplasts filled with red and yellow carotenoids, respectively. Examples of such carotenoids are capsanthin and capsorubin (red) and violaxanthin and zeaxanthin (yellow). The different possible colors of the mature and non-mature fruits are usually a combination of different ratios between the red, green and yellow color components.

In literature, at least two loci were described to be involved in the color development of the fruits of the genus *Capsicum* designated the Y and CL loci.

The locus Y controls the development of a red color component in the fruits. Plants comprising the dominant Y allele have fruits with a red color component and plants comprising two recessive y alleles lack a red color component. In detail, plants of the genotype Y/Y, Y/y and y/Y have the phenotypical fruit trait red color component and plants of the genotype y/y do not have a red color component.

The Y and y alleles separate in a Mendelian fashion in crosses i.e. independent of other phenotypical traits, indicating the involvement of a single gene.

The difference between the Y allele and the y allele is a deletion, rearrangement or mutation of a region approximately 25 cM away from the RFLP (Restriction Fragment Length Polymorphism) marker CT204. Recently, it was demonstrated in crosses that the Y locus cosegregates with a gene encoding the enzyme capsanthin-capsorubin synthase (CSS). The enzyme capsanthin-capsorubin synthase (CSS) is involved in the synthesis of red carotenoid pigments in the fruits of plants of the genus *Capsicum*. Since the location of the capsanthin-capsorubin synthase gene is a genomic region, 25 cM away from the RFLP (Restriction Fragment Length Polymorphism) marker CT204, it is generally accepted that the capsanthin-capsorubin synthase (CSS) gene is the gene responsible for the trait Y, observed in classic breeding experiments.

The locus CL is involved in the transformation of chloroplasts to chromoplasts in plants of the genus *Capsicum*. During maturation of the fruits, the chlorophyl, responsible for the green color of the fruits, is degraded and the synthesis of carotenoids is initiated. The CL allele is dominant and the cl allele is recessive. Plants of the genotype CL/CL, CL/cl and cl/CL all have the phenotype that the chloroplasts are transformed into chromoplasts in contrast with the genotype cl/cl whereby the chloroplasts are maintained usually resulting in a lasting green color of the matured fruits.

It was shown that this locus also inherited independently in a Mendelian fashion indicating the involvement of a single gene. However, until now, neither the position of the CL locus on a physical genomic map, nor the specific gene involved in this phenotype could be determined.

In most countries, like the United States and Mexico, the most abundant color of harvested fruits of plants of the genus *Capsicum* like peppers is green. Every year, in the United states approximately 40.000 ha peppers are harvested green and in Mexico 80.000 ha peppers are harvested green. In general, one can state that most peppers are harvested green and there is a worldwide preference for eating and processing green peppers especially for the preparation of food products.

Although most peppers are consumed while they are still non-matured and thus usually green, the taste of these green non-mature peppers is regarded "less" than the taste of mature peppers, like yellow and red peppers. This is due to the lower sugar content in the non-mature green fruits as compared to the mature fruits. Because of the higher sugar content in mature fruits these fruits are regarded as "tasting" better, i.e. more sweet.

It is therefore a goal of the present invention to improve the taste, i.e. sweetness, of the green fruits of plants belonging to the genus *Capsicum*.

Peppers are an important source of ascorbic acid (vitamin C) in the human diet. Ascorbic acid is essential for the synthesis of collagen, one of the most abundant proteins in the human body. Additionally, ascorbic acid is important for the inactivation of free radicals, which are byproducts of the oxidation pathways, and thus important for the prevention of a number of diseases amongst which cancer.

Most people regard oranges as the most abundant source of ascorbic acid, and therefore the fruits of choice for the daily intake of this important vitamin.

Peppers comprise per kilogram fresh weight at least three times more ascorbic acid than oranges and are therefore better suited as a daily source of ascorbic acid. However, Peppers are usually consumed as a "taste" providing ingredient in food products and thus usually not used in quantities sufficient for the daily intake of ascorbic acid. Fruits of the genus *Capsicum* comprising a higher ascorbic acid content would provide an improved source of this vitamin even in lower quantities.

It is therefore a second goal of the present invention to provide fruits of plants of the genus *Capsicum* with enhanced nutritional value, i.e. increased concentrations of ascorbic acid, compared to other plants of the genus *Capsicum*.

In the research that lead to the present invention, the inventors surprisingly found that the above-mentioned two loci, Y and CL, which were previously only identified to be involved in color traits, are also responsible for other unexpected phenotypical traits involving the sugar and ascorbic acid content in fruits of plants of the genus *Capsicum*.

Therefore the above-stated goals of the present invention, improved taste and increased nutritional value, are provided by the method disclosed in claim 1 of the present invention involving the two loci CL and Y.

The method according to claim 1 improves the taste and/or the nutritional value of fruits of a plant belonging to the genus *Capsicum*, by manipulation of the CL and the Y loci preferably resulting in a plant of the genus *Capsicum*, comprising two recessive y alleles and two recessive cl alleles.

A plant comprising the genotype y/y, cl/cl can be obtained in a number of ways such as using parent plants which comprise a y allele and/or a cl allele.

Since in most cases the presence of a y allele can not directly be determined from the phenotype, by for example color determination of the fruits, due to the dominant nature of a Y allele and the involvement of multiple genes in color development, biological analysis methods, like biochemical and molecular biological methods, are preferably used to determine the presence of a y allele. For similar reasons, a recessive trait and multiple genes, the presence of a cl allele is also preferably determined by using these biological analysis methods.

A parent plant comprising a y allele can for example be selected by using RFLP (Restriction Length Polymorphism). In detail, the genomic DNA of plants of the genus *Capsicum* can be digested with a restriction enzyme, like Dral, and after gel separation of the fragments, the presence of a polymorphism can be detected with for example a probe recognizing the genomic sequence of the capsanthin-capsorubin synthase (CSS) gene.

The presence of a y allele is indicated by a different sized band on for example a Southern blot as compared with the band indicating the presence of a Y allele. Depending on the nature of the polymorphism, like a deletion, a rearrangement, a mutation, or an insertion, the size of the band indicating the presence of the y allele will be larger or smaller in size. It is well within the skills of the person skilled in the art by using the phenotype of the Y locus and classical breeding methods to determine which band indicates the y allele.

The presence of a y allele can also be detected by PCR using primers annealing to the 5' end and 3' end of the capsanthin-capsorubin synthase (CSS) gene (GenBank accession number X77289). Plants comprising the y allele are identified by a different sized (compared to the amplification product of the Y allele) specific amplification product.

In addition to identification of a parent plant, an inactivation or inhibition of the capsanthin-capsorubin synthase (CSS) gene and thus a plant comprising a y allele can also be achieved using modern biotechnological methods such as RNA silencing, knock-out, knock-in, anti-sense etc.

Since the chromosomal location nor the gene corresponding to the CL locus is known, a parent plant comprising the cl allele can be identified by selection of plants of the genus *Capsicum* comprising intact chloroplasts or chromoplasts still comprising chlorophyl in the mature fruits. The presence of chloroplast or chromoplasts comprising chlorophyl in mature fruits can be confirmed by using microscopy or staining techniques for chlorophyl or chlorophyl content analysis like for example HPLC analysis.

After selection of (a) parent plant(s) comprising the y allele and the cl allele, a plant with the genotype y/y, cl/cl can easily be obtained by using classical breeding techniques generally known to the person skilled in the art. For example, starting from parent 1 (genotype Y/Y, cl/cl; brown fruits) and parent 2 (genotype y/y, CL/CL; yellow fruits) the offspring ($F_1$) will be genotype Y/y, CL/cl. A plant with a genotype y/y, cl/cl can be obtained by a selfing of the $F_1$. Genetics predicts that the $F_1$ will comprise 1 out of 16 plants of the y/y, cl/cl genotype.

Plants comprising the genotype y/y, cl/cl are green both in the non-mature and in the mature phase of the fruits. Since the green color of peppers is preferred, such plants also provide for commercial reasons an advantage.

In one preferred embodiment of the invention, the recessive Y locus (y/y) is derived from a plant chosen from the group consisting of *Capsicum annuum*, *Capsicum baccatum*, *Capsicum frutescens*, *Capsicum chinense*, and *Capsicum chacoense*, preferably *Capsicum annuum*. These species are the most commonly used breeds and in addition can easily be crossed amongst each other, thus facilitating obtaining a plant with the genotype y/y;cl/cl after selection of the appropriate parent plant(s).

For similar reasons, the recessive CL locus (cl/cl) is derived from a plant chosen from the group consisting of *Capsicum annuum*, *Capsicum baccatum*, *Capsicum frutescens*, *Capsicum chinense*, and *Capsicum chacoense*, preferably *Capsicum annuum*.

The plants according to the present invention are characterized by an enhanced sugar content in the fruits of the plant relative to the fruits of similar type plants of the genus *Capsicum*. The higher sugar content in the fruits of plants comprising the y/y;cl/cl genotype, especially in the non-mature phase, provides that the "taste" of such fruits is sweeter as compared to the "taste" of similar type fruits comprising another genotype by increasing the sucrose content by at least a factor 1.5.

More specifically, the plants according to the invention are characterized by a sucrose content of the fruits of more than 5, preferably 5.0, 5.3, 5.6, 5.9, 6.2, 6.3, 6.5, 6.9, 7.1, 14.9, 20.1, 23.4, 25, 30, 35, 40 thus 5 to 40, more preferably 5.4, 5.6, 5.9, 6.2, 6.3, 6.5, 6.6, 6.9, 7.1, 13.5, 14.4, 15.4, or 16.8 thus 5.4 to 16.8 grams per kilogram fresh weight.

The plants according to the invention, comprising the y/y;cl/cl genotype are also characterized by an enhanced ascorbic acid content in the fruits of the plant relative to similar type fruits, of any color, of other plants of the genus *Capsicum*. The higher ascorbic acid content of the fruits by at least a factor 1.3 is especially apparent in the matured fruits.

In more detail, the plants according to the present invention are characterized by an ascorbic acid content of the fruits higher than 2.0, preferably 2.0, 2.3, 2.4, 2.5, 3.6, 4.8, 5.0, 6.5, or 7 thus 2.0 to 7, more preferably 2.1, 2.2, 2.3, 2.4, 2.5, 2.6, 2.7, 2.85 thus 2.1 to 2.85 grams per kilogram fresh weight.

In another preferred embodiment of the present invention the plants are two commercially available breeds designated "Evergreen 7181", "Evergreen 6203".

The plants of the genus *Capsicum* with green fruits comprising the genotype y/y;cl/cl, provided by the method according to the present invention, posses advantageous characteristics, like taste and nutritional value, compared to other peppers according to the prior art. Thus the present invention also relates to fruits of plants of the genus *Capsicum* obtainable with the above-described method. It is obvious to also seeds, seedlings and any plant parts comprising the genotype y/y;cl/cl are encompassed by the present invention.

The fruits according to the present invention can be used for a number of applications. The fruits are particularly useful for the preparation of food products like salads, sauces and other processed foods. In general, green, non-mature paprika's are used for these applications and the use of the fruits according to the present invention will improve the taste and the nutritional value of these food products.

The invention will be further illustrated by the following examples which are not intended to limit the scope of the invention but are only presented to illustrate the invention, whereby reference is made to the following figures.

FIGURES

FIG. 1. Plot illustrating the increased sucrose content in plants comprising the genotype y/y;cl/cl as compared to other plants of a similar type.

Figure 2:
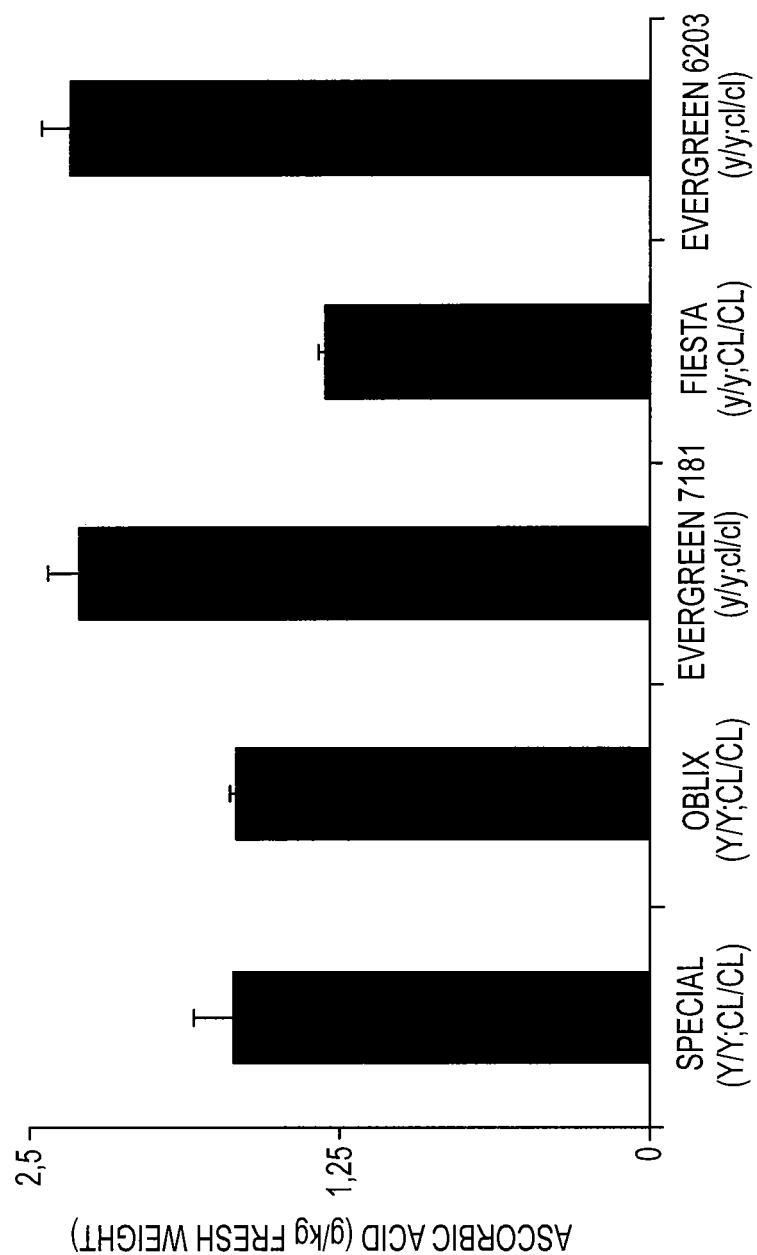

FIG. 2. Plot illustrating the increased ascorbic acid content in plants comprising the genotype y/y;cl/cl as compared to other plants of a similar type.

EXAMPLES

Example 1

Analysis of the Sucrose Content of Peppers Comprising Different Y and CL Loci

The genotype of 5 different peppers was determined, designated "Special", "Oblix", "Evergreen 7181", "Fiesta", and "Evergreen 6203". The peppers comprised the following genotypes, Y/Y;CL/CL, Y/Y;CL/CL, y/y;cl/cl, y/y;CL/CL, and y/y;cl/cl respectively. Plants were grown and fruits were harvested. The sucrose content in the fruits was determined by the following method.

Plant material was grounded in liquid nitrogen into a fine powder. 0.25 gram of frozen material was weighed and mixed with 4 ml of ice-cold 5% meta-phosphoric acid containing 1 mM diethylenepenta-acetic acid. After sonication for 15 minutes and filtration over a 0.2 μm Teflon filter, 150 mg fresh weight of frozen powder was extracted with 1.5 ml of water at 85° C. for 30 min, centrifuged for 5 min at 20000 g, and supernatant was collected. The pellet was once re-extracted using the above-described conditions. Supernatants were pooled and stored frozen for further analysis.

For analysis, the samples were diluted 10, 50 or 100 times before injection (in order to obtain a signal in the linear range of the detector). Quantification was performed by comparison with external standards. Analysis was performed as described in Sevenier et al. 1996 (*Nat. Biotech.*, 1998, 16: 843-846) with detector settings according to Dionex instructions for carbohydrate (Dionex technical note 21) The obtained results are summarized in table 1

TABLE 1

| SUCROSE (grams per kilogram fresh weight) | | | | |
|---|---|---|---|---|
| VARIETY | A | B | mean | SD |
| Special | 4.4 | 4.0 | 4.2 | 0.3 |
| Oblix | 4.3 | 2.1 | 3.2 | 1.6 |
| Evergreen 7181 | 6.6 | 5.9 | 6.3 | 0.5 |
| Fiesta | 3.3 | 2.1 | 2.7 | 0.8 |
| Evergreen 6203 | 6.2 | 6.3 | 6.3 | 0.1 |

Table 1 is graphically presented in FIG. 1.

From table 1 and FIG. 1 it is clear that peppers comprising the y/y, cl/cl genotype contain a higher sucrose content than peppers comprising another genotype. The difference in sucrose content can be as high as more than 1.5 fold depending on the variety used, thus providing peppers with improved "taste".

Example 2

Analysis of the Ascorbic Acid Content of Peppers Comprising Different Y and CL Loci The different genotypes described in the above-given example 1 were also tested for their ascorbic acid content. Plants were grown and the fruits were harvested The ascorbic acid content was determined by the following method Plant material was grounded in liquid nitrogen into a fine powder. 0.25 g of frozen material was weighed and mixed with 4 ml of ice-cold 5% meta-phosphoric acid containing 1 mM diethylenepenta-acetic acid. After sonication for 15 minutes and filtration over a 0.2 μm Teflon filter, 10 μl was injected into a Waters Alliance HPLC system equipped with a photodiode array detector (Waters 996). Ascorbic acid was eluted with 50 mM potassium phosphate pH 4.4 at 0.5 ml/min using a YMC-Pro C18 150×3.9 mm column set at 30° C. A calibration curve was recorded using a standard curve of free ascorbic acid dissolved in the extraction solution. Recovery of ascorbic acid standard added to the tissues just before extraction was more than 95%, while reproducibility of extraction and analyses of tissues was better than 90%. The obtained results are summarized in table 2

TABLE 2

| ASCORBIC ACID (grams per kilogram fresh weight) | | | | |
|---|---|---|---|---|
| VARIETY | A | B | mean | SD |
| Special | 1.56 | 1.79 | 1.68 | 0.16 |
| Oblix | 1.70 | 1.67 | 1.68 | 0.02 |
| Evergreen 7181 | 2.39 | 2.22 | 2.31 | 0.12 |
| Fiesta | 1.28 | 1.32 | 1.30 | 0.03 |
| Evergreen 6203 | 2.26 | 2.40 | 2.33 | 0.12 |

Table 2 is graphically presented in FIG. 2.

From table 2 and FIG. 2 it is clear that peppers comprising the y/y, cl/cl genotype contain a higher ascorbic acid content than peppers comprising another genotype. The difference in ascorbic acid content can be as high as more than 1.5 fold thus providing peppers with improved nutritional value.

DEPOSIT INFORMATION

A deposit of the hybrid pepper 'Evergreen 6203' is maintained by Enza Zaden Beheer B. V., having an address at Haling le, Enkhuizen, 1602 DB, The Netherlands. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety with the American Type Culture Collection, (ATCC), ATCC Patent Depository, 10801 University Boulevard, Manassas, Va., 20110, USA.

At least 2500 seeds of hybrid pepper 'Evergreen 6203' were deposited on Mar. 31, 2014 according to the Budapest Treaty in the American Type Culture Collection (ATCC), ATCC Patent Depository, 10801 University Boulevard, Manassas, Va., 20110, USA. The deposit has been assigned ATCC number PTA-121139. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed.

A deposit of the hybrid pepper 'Evergreen 7181' is maintained by Enza Zaden Beheer B. V., having an address at Haling le, Enkhuizen, 1602 DB, The Netherlands. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety with the American Type Culture Collection, (ATCC), ATCC Patent Depository, 10801 University Boulevard, Manassas, Va., 20110, USA.

At least 2500 seeds of hybrid pepper 'Evergreen 7181' were deposited on Mar. 31, 2014 according to the Budapest Treaty in the American Type Culture Collection (ATCC), ATCC Patent Depository, 10801 University Boulevard, Manassas, Va., 20110, USA. The deposit has been assigned ATCC number PTA-121140. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed.

The deposits will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:

1. Hybrid pepper seed designated as 'Evergreen 6203', representative sample of seed having been deposited under ATCC Accession Number PTA-121139.

2. A pepper plant produced by growing the seed of claim 1.

3. A plant part from the plant of claim 2.

4. The plant part of claim 3, wherein said part is a pepper fruit.

* * * * *